United States Patent
Niyiro et al.

(10) Patent No.: US 6,447,817 B1
(45) Date of Patent: Sep. 10, 2002

(54) ANTI-INFLAMMATORY ANALGESIC

(75) Inventors: Yasunori Niyiro, Fujinomiya (JP); Shigeru Koda, Shizuoka (JP); Satoru Sugiyama, Nagoya (JP)

(73) Assignee: Nippon Hypox Laboratories Inc., Tokyo (JP)

( * ) Notice: Subject to any disclaimer, the term of this patent is extended or adjusted under 35 U.S.C. 154(b) by 0 days.

(21) Appl. No.: 09/744,299

(22) PCT Filed: Aug. 10, 1999

(86) PCT No.: PCT/JP99/04308

§ 371 (c)(1),
(2), (4) Date: Jan. 23, 2001

(87) PCT Pub. No.: WO00/09121

PCT Pub. Date: Feb. 24, 2000

(30) Foreign Application Priority Data

Aug. 10, 1998 (JP) ............................................ 10-259088

(51) Int. Cl.⁷ ................................................ A61K 35/78
(52) U.S. Cl. .................... 424/742; 424/78.05; 424/725; 424/747; 435/166; 435/410; 514/474; 514/168
(58) Field of Search ........................... 424/78.02, 78.05, 424/78.07, 725, 742, 747; 514/816, 817, 886, 887, 474, 168

(56) References Cited

U.S. PATENT DOCUMENTS 4,636,520 A * 1/1987 Umio et al.
5,073,366 A * 12/1991 Beck
5,194,445 A * 3/1993 Satoh et al.
5,780,458 A * 7/1998 Blank

FOREIGN PATENT DOCUMENTS

| JP | 57-24308 | | 2/1982 |
| JP | 282488 | * | 9/1986 |
| JP | 62-87509 | | 4/1987 |
| JP | 2-209807 | | 8/1990 |
| JP | 9-12450 | | 1/1997 |

* cited by examiner

Primary Examiner—Leon B. Lankford, Jr.
Assistant Examiner—Ruth A. Davis
(74) Attorney, Agent, or Firm—Nixon & Vanderhye P.C.

(57) ABSTRACT

The present invention is concerned with an anti-inflammation analgesic preparation which contains a specific 3-0-substituted ascorbic acid as an active ingredient, shows excellent anti-inflammation analgesic effects and is excellent in shelf life, safety to a skin and endermic absorptivity of the active ingredient.

2 Claims, No Drawings

ANTI-INFLAMMATORY ANALGESIC

TECHNICAL FIELD

The present invention relates to an anti-inflammation analgesic preparation. More specifically, it relates to an anti-inflammation analgesic preparation which exhibits an excellent anti-inflammation analgesic effect on pains involving a swelling of a muscle, a joint or a bone and a fatigue involving lassitude and which is excellent in a shelf life, safety to a skin and endermic absorptivity of an effective ingredient.

TECHNICAL BACKGROUND

It has been found that a cyclooxygenase inhibitor is useful in an anti-inflammation analgesic preparation, and since then, a variety of anti-inflammation analgesic preparations containing a cyclooxygenase inhibitor have been proposed. At present, however, on the basis of any cyclooxygenase inhibitor, there has been obtained no satisfactory anti-inflammation analgesic preparation which is free from side effects and useful against lumbago, bruise, sprain, stiff shoulder, arthralgia, myalgia, a swelling and a pain after muscle fatigue or bone fracture, shoulder periarthritis, tendon-thecitis, peritendinitis, inflammation of lateral epicondyle of humerus, a swelling after injury, an ache, a swelling and a pain from rheumatism or osteoarthritis and a pain and fatigue of a leg and loins from excess exercise or labor.

Meanwhile, ascorbic acid has been studied with regard to its various physiological activities and is well recognized to be a vitamin indispensable for keeping health. It is clear from many reports that it is useful for strengthening a blood vessel wall due to promotion of the biosynthesis of glucocorticoids which are distributed in adrenal gland to a greater extent and are anti-inflammation factor in oroganisms or the synthesis of collagen. However, there has been completed no technique to utilize ascorbic acid in an anti-inflammation analgesic preparation, since ascorbic acid is readily decomposed upon contact to light, heat, water and metal ion or has a problem on endermic absorptivity.

Clearly, prostaglandins derived from cyclooxygenase play a great part in proceeding of an inflammation and are useful for an effect on relieving some pains and decreasing some inflammations. However, a typical cyclooxygenase inhibitor, indomethacin, fails to satisfy an expectation regardless of whether it is orally administered or endermicly applied. In treatment of a rheumatic patient in particular, it is used as a supplementary drug for avoiding side effects caused by a gold preparation or a steroid preparation, or it is used for a patient whose disease condition is moderate. Nonsteroidal anti-inflammation preparations typified by indomethacin and mefenamic acid are orally used for decreasing inflammation and relieving pains after surgical treatments of bone fracture or tooth extraction. However, they are not satisfactory since they are recognized not only to have side effects such as disorders on a stomach or duodenum but also to have side effects such as rubefaction, itching, eruption, irritation and the like.

DISCLOSURE OF THE INVENTION

Under the circumstances the present inventors have made diligent studies and as a result have found that a drug containing a specific ascorbic acid derivative as an active ingredient has remarkably high anti-inflammation analgesic activities and is excellent in stability and safety and that such a drug is further excellent in endermic absorptivity. While it has been already pointed out that an ascorbic acid has an anti-inflammation analgesic effect, there is no example of practical use thereof for a reason that it is poor in stability, safety and endermic absorptivity as described above.

Further, the present inventors have also made studies concerning how to apply the active ingredient and have found that therapy by external use of the specific ascorbic acid derivative is more useful for attaining the object, and the present invention has been accordingly completed.

It is an object of the present invention to provide an anti-inflammation analgesic preparation useful against lumbago, bruise, sprain, stiff shoulder, arthralgia, myalgia, a swelling and a pain after muscle fatigue or bone fracture, rheumatism or osteoarthritis and a swelling, edema and stiffness from exercise or physical fatigue.

The anti-inflammation analgesic preparation of the present invention for achieving the above object comprises an ascorbic acid derivative of the following formula (I) or a salt thereof,

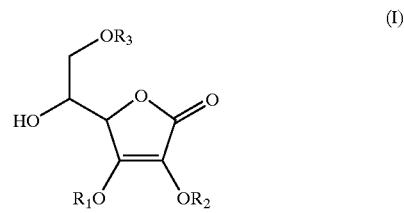

(I)

wherein at least one of $R_1$, $R_2$ and $R_3$ is a linear or branched alkyl group having 1 to 20 carbon atoms, an alkylcarbonylmethyl, an alkoxycarbonylmethyl, an allylalkyl, an acyl, a sulfonic acid group or a phosphoric acid group, and the rest represents hydrogen.

Of ascorbic acid derivatives of the formula (I), a 3-0-substituted ascorbic acid of the formula (II) in particular is excellent in effectiveness, stability, safety and endermic absorptivity and is suitable for use as an anti-inflammation analgesic preparation for external application.

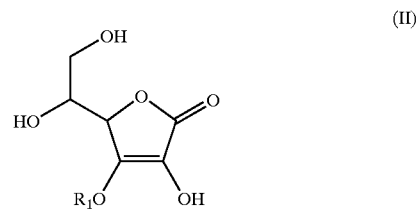

(II)

wherein $R_1$ is a linear or branched alkyl group having 1 to 20 carbon atoms, an alkylcarbonylmethyl or an alkoxycarbonyl methyl.

The 3-0-substituted ascorbic acid of the formula (II) used in the present invention is a known ascorbic acid derivative which generally has anti-oxidative activity and is recognized to have carcinogenesis inhibition activity, cancer-metastasis prevention activity, fair skin making activity. Further, WO91/03471 refers to an organ-disorder inhibition activity based on inhibition activity against a lipid peroxidation.

The 3-0-substituted ascorbic acid of the formula (II) includes 3-0-alkylascorbic acid ($R_1$=alkyl), 3-0-alkylcarbonylmethylascorbic acid ($R_1$= alkylcarbonylmethyl) and 3-0-alkoxycarbonylmethylascorbic acid ($R_1$= alkoxycarbonylmethyl).

First, the 3-0-alkylascrobic acid includes L-3-0-methylascorbic acid, L-3-0-ethylascorbic acid, D-3-0-ethylascorbic acid, L-3-0-propylascorbic acid, L-3-0-isopropylascorbic acid, L-3-0-butylascorbic acid, L-3-0-isobutylascorbic acid, L-3-0-pentylascorbic acid, L-3-0-hexylascorbic acid, L-3-0-octylascorbic acid, L-3-0-decylascorbic acid, L-3-0-dodecylascorbic acid, L-3-0-tetradecylascorbic acid, L-3-0-hexadecylascorbic acid, L-3-0-octadecylascorbic acid and L-3-0-didecylascorbic acid.

The 3-0-alkylcarbonylmethylascorbic acid includes L-3-0-methylcarbonylmethylascorbic acid, L-3-0-ethylcarbonylmethylascorbic acid, L-3-0-butylcarbonylmethylascorbic acid, L-3-0-hexylcarbonylmethylascorbic acid, L-3-0-octylcarbonylmethylascorbic acid, L-3-0-decylcarbonylmethylascorbic acid, L-3-0-dodecylcarbonylmethylascorbic acid, L-3-0-tetradecylcarbonlmethylascorbic acid, L-3-0-hexadecylcarbonylmethylascorbic acid, L-3-0-octadecylcarbonylmethylascorbic acid and L-3-0-didecylcarbonylmethylascorbic acid.

The 3-0-alkoxycarbonylmethylascorbic acid includes L-3-0-methoxycarbonylmethylascorbic acid, L-3-0-ethoxycarbonylmethylascorbic acid, L-3-0-butoxycarbonylmethylascorbic acid, L-3-0-hexyloxycarbonylmethylascorbic acid, L-3-0-octyloxycarbonylmethylascorbic acid, L-3-0-decyloxycarbonylmethylascorbic acid, L-3-0-dodecyloxycarbonylmethylascorbic acid, L-3-0-tetradecyloxycarbonylmethylascorbic acid, L-3-0-hexadecyloxycarbonylmethylascorbic acid, L-3-0-octadecyloxycarbonylmethylascorbic acid and L-3-0-didecyloxycarbonylmethylascorbic acid.

These ascorbic acid derivatives can be synthesized by a known method described in JP-A-1-228977 or the like.

The present invention may use L-ascorbic acid-2-phosphate ester and a salt thereof, ascorbic acid-2-sulfate ester, L-ascorbic acid-2-pyrophosphoric acid, L-6-0-stearylascorbic acid, L-6-0-palmitoylascorbic acid, L-2,6-0-dipalmitoylascorbic acid or L-ascorbic acid-2-glycoside included in the ascorbic acid derivative of the formula (I).

Together with the above ascorbic acid derivative, the anti-inflammation analgesic preparation of the present invention may contain at least one secondary ingredient selected from a salicylic acid derivative, indomethacin, piroxicam, flurbiprofen, felbinac, ketoprofen, menthol, camphor, thymol, crotamiton or eucalyptus oil. The secondary ingredient improves the ascorbic acid derivative in endermic absorptivity and has an additional effect on overcoming a usual stiff shoulder or muscle fatigues regardless of disease conditions.

Specific examples of the salicylic acid derivative include salicylic acid, methyl salicylate, propyl salicylate, butyl salicylate, glycol salicylate and sodium salicylate.

When the anti-inflammation analgesic preparation of the present invention is used for an external skin, the amount of the active ingredient is preferably 0.01 to 50% by weight, more preferably in the range of from 0.1% to 10.0%, although the amount shall not be limited thereto. When the above amount is less than 0.01% by weight, it is difficult to obtain the effect. When it exceeds 50% by weight, undesirably, no further effect corresponding to an additional content can be observed.

The preparation form of the anti-inflammation analgesic preparation of the present invention can be properly selected depending upon types and degrees of diseases for which the preparation is used and ages of patients. When the preparation is administered orally, a powder, granules, a tablet, a capsule, a troche or a liquid is preferred in view of determination of a dosage and simplicity in use. When it can be applied directly to a diseased part, an injection preparation or a preparation for an external skin is preferred in view of prompt working and safety. The above preparation for an external skin can be used in any preparation form so long as it is among preparations used for an external skin such as a cosmetic, a medicament or a non-medicament product.

As examples, the preparation form includes a broad range of forms such as an aqueous solution lotion, a soluble lotion, a suspension lotion, a water-oil separate lotion, an emulsion, a cream, a pack, a paste, a poultice, a stick, an ointment, a plaster, a liniment and a tape.

The anti-inflammation analgesic preparation of the present invention may contain other component(s) used in medicaments or cosmetics in addition to the above essential ingredient so long as the effect of the present invention is not impaired. Specific examples thereof are as follows.

Powder components such as starch, lactose, dextrin, talc, silicone, nylon, cellulose, etc., oil components such as avocado oil, corn oil, olive oil, rape oil, evening primrose oil, castor oil, sunflower seed oil, tea seed oil, rice bran oil, jojoba oil, cacao oil, coconut oil, squalane oil, beef tallow, lard, Japan wax, beeswax, candelilla wax, carnauba wax, spermaceti, lanolin, silicone oil, fluorine oil, liquid paraffin, sericin, petrolatum, polyoxyethyleneoleyl alcohol ether, glycerin ethylhexanoate, pentaerythritol ethylhexanoate, cetyl ethylhexanoate, glyceryl monooleate, etc., higher alcohols such as capryl alcohol, lauryl alcohol, myristyl alcohol, cetyl alcohol, etc., higher fatty acids such as caprylic acid, lauric acid, myristic acid, palmitic acid, stearic acid, behenic acid, lanolin fatty acid, linoleic acid, linolenic acid, etc., moisturizers such as polyethylene glycol, glycerin, sorbitol, xylitol, maltitol, lactic acid, urea, hyaluronic acid, natural moisturizing factor (NMF), pyrrolidonecarboxylic acid, ceramide, etc., thickeners such as methylcellulose, ethylcellulose, gum Arabic, alginic acid, carboxyvinyl polymer, polyvinyl alcohol, montmorillonite, raponite, etc., organic solvents such as ethanol, etc., antioxidants such as butylhydroxyanisole, butylhydroxytoluene, tocopherol, phytic acid, ferulic acid, etc., antifungal antiseptics such as salicylic acid, p-oxybenzoic acid alkyl ester (ethylparaben, butylparaben, etc.), hexachlorophene, etc., lower organic acids used as an alimental component for a skin such as α-hydroxyacids such as lactic acid, tartaric acid, citric acid, glycolic acid, etc., and salts of these, vitamins such as retinol palmitate or vitamin A and derivatives thereof, β-carotene and derivatives thereof, vitamin B2 and derivatives thereof, vitamin B6 and derivatives thereof, vitamin B12 and derivatives thereof, niacins and derivatives thereof, tocopherol and derivatives thereof, γ-oryzanol and derivatives thereof, vitamin D and derivatives thereof, vitamin H, pantothenic acid, pantethine, pantothenyl alcohol, etc., components for a skin or medicated components for a skin such as allantoin, caffeine, resorcin, hydroquinone, glycyrrhetic acid and derivatives thereof, kojic acid and derivatives thereof, glabridin and derivatives thereof, hinokitiol, mucidin, bisabolol, eucalyptol, inositol, panthenyl ethyl ether, saponins (bupleurum root saponin, loofah saponin, soapberry saponin, etc.), royal jelly, ethynylestradiol, cepharanthine, photosemsitizer, tranexamic acid, azulene and derivatives thereof, ubiquinones, steroidal anti-inflammation agents, etc., squeezed products or dry products which are prepared, by any method, from plants as raw materials such as aloe, licorice, mulberry bark, artemisia capillaris spica, phellodendron bark, scutellaria root, horse chestnut, Sophora root, rosemary, clove, crataegus fruit, horse chestnut, fennel, orange, lemon, avocado, kiwi fruit, peach, cucumber, eggplant, tomato, carrot, saxifrage, loofah, sage, thyme, mint, birch, bitter orange peel, Japanese angelica root, lily, mugwort, strawberry, grape, pineapple, apple, Angelica keiskei, banana, oarweed, "wakame" (Laminaria Undaria), Algecolloid, arnica, lettuce, cabbage, grape fruit, mangosteen, papaya, litchi, etc., solid, semi-solid or liquid extracts obtained by extraction of these in water, an alcohol or an aqueous alcohol and not defined in the scope of the present invention, anionic surfactants such as sodium laurylsulfate, polyoxyethylene laurylsulfate triethanolamine, dioctyl sulfosuccinate ester, higher alcohol phosphate ester, etc., cationic surfactants such as benzethonium chloride, cetylpyridinium chloride, benzalkonium chloride, etc., nonionic surfactants such as glycerin higher fatty acid ester, sorbitan higher fatty acid ester, polyoxyethylene polyhydric alcohol fatty acid ester, sucrose fatty acid ester, polyoxyethylene alkyl ether, polyoxyethylene alkylphenyl ether, etc., metal blockers such as lactoferin, edetic acid and derivatives or salts thereof, and perfumes.

The present invention will be explained further in detail with reference to Examples and Comparative Examples, while the present invention shall not be limited thereto. "%" stands for "% by weight".

TEST EXAMPLE 1

For clarifying the effect of the anti-inflammation analgesic preparation of the present invention, the effect of the anti-inflammation analgesic preparation on inhibition of serotonin swelling is shown below.

1.5 Grams of a 2% xanthan gum solution containing a test sample of having a concentration of 3% was applied to a portion ranging from a right femoral portion to a sole portion (bottom portion) of a rat. Two hours after the test sample was applied, a solution of 3 $\mu$g/ml of serotonin in 0.1 ml of a saline solution was hypodermically injected into the sole of the right foot. Thirty minutes after the injection of the inflammatory substance, the swelling of the sole of the right leg was measured to determine a swelling ratio. When serotonin as an inflammatory substance involving the generation of a pain is injected, a swelling involving a pain is caused. A 3% bendazac as one example of known anti-inflammation analgesic preparations for a skin failed to inhibit the above inflammation reaction. In contrast, when the ascorbic acid derivative of the present invention was applied, the swelling was strongly inhibited. Table 1 shows the results.

TABLE 1

Activity against serotonin swelling of rat

| Test Example | Test Compound | Average swelling ratio (%) | Average inhibition ratio (%) |
|---|---|---|---|
| (1) | L-ascorbic acid-2-phosphoric acid ester magnesium salt | 28 | 7 |
| (2) | L-3-0-ethylascorbic acid | 12 | 76 |
| (3) | L-3-0-dodecylascorbic acid | 14 | 54 |
| (4) | L-3-0-dodecylcarbonyl-methylascorbic acid | 13 | 57 |
| (5) | L-3-0-octadecyloxy-carbonylmethylascorbic acid | 15 | 50 |
| Comparative Example | Bendazac | 30 | 0 |
| — | Control | 30 | — |

As clearly shown in Table 1, in Test Examples (1) to (5) using the ascorbic acid derivatives of the present invention, the serotonin swelling was strongly inhibited, and the ascorbic acid derivatives of the present invention were effective for producing the anti-inflammation effect. On the other hand, the commercially available anti-inflammation analgesic preparation, 3% bendazac ointment, showed no effect on the swelling and was ineffective.

Preparation Example 1

| Xanthan gum | 1% |
|---|---|
| L-3-0-ethylascorbic acid | 3% |
| Ethanol | 10% |
| Methylparaben | 0.2% |
| L-menthol | 1.0% |
| Purified water | Balance |

L-3-0-Ethylascorbic acid, methylparaben and L-menthol were weighed, ethanol was added, and these were mixed. This solution was added to, and mixed with, a xanthan gum aqueous solution, and these solutions were totally homogenized to obtain a product.

Preparation Example 2

| L-3-0-dodecylascorbic acid | 4% |
|---|---|
| Ethanol | 10% |
| methyl salicylate | 0.2% |
| Hydrophilic ointment | Balance |

L-3-0-Dodecylascorbic acid and methyl salicylate were weighed, ethanol was added, and these were mixed. This solution and a hydrophilic ointment were mixed and totally homogenized to obtain a product.

Preparation Example 3

| L-3-0-octadecyloxycarbonylmethylascorbic acid | 5% |
|---|---|
| Ethanol | 10% |
| Methylparaben | 0.2% |
| L-menthol | 1.0% |
| Hydrophilic ointment | Balance |

L-3-0-Octadecyloxycarbonylmethylascorbic acid and L-menthol were weighed, ethanol was added, and these were mixed. This solution and a hydrophilic ointment were mixed and totally homogenized to obtain a product.

Preparation Example 4

| L-3-0-Dodecylcarbonylmethylascorbic acid | 5% |
|---|---|
| Ethanol | 10% |
| Methylparaben | 0.2% |
| Thymol | 1.0% |
| xanthan gum | 2.0% |

L-3-0-Dodecylcarbonylmethylascorbic acid, methylparaben and thymol were weighed, ethanol was added, and these were mixed. This solution was added to a xanthan solution, and these were mixed and totally homogenized to obtain a product.

Comparative Preparation Example 1

| | |
|---|---|
| Xanthan gum | 1% |
| Ethanol | 10% |
| Methylparaben | 0.2% |
| Methyl salicylate | 0.2% |
| Purified water | Balance |

Preparation Example 2 was repeated except that the ascorbic acid derivative of the present invention was not used, to prepare a comparative gel.

Comparative Preparation Example 2

| | |
|---|---|
| Ethanol | 10% |
| Methylparaben | 0.2% |
| L-menthol | 1.0% |
| Hydrophilic ointment | Balance |

Preparation Example 3 was repeated except that the ascorbic acid derivative of the present invention was not used, to prepare a comparative cream.

TEST EXAMPLE 2

For clarifying the effect of the anti-inflammation analgesic preparation of the present invention, each of the anti-inflammation analgesic preparations of the present invention obtained in the above Preparation Examples 1 to 4 and the comparative anti-inflammation analgesic preparations obtained in Comparative Preparation Examples 1 and 2 was provided to 10 people for applying them twice a day, morning and evening, for approximately one month, and the ten people were requested to give results with regard to activities against the lassitude of arms and legs and stiff shoulders. Table 2 shows the results.

TABLE 2

| | Anti-inflammation analgesic effects for human | | | |
|---|---|---|---|---|
| | Lassitude of arms and legs | | Stiff shoulder | |
| | Effective | Ineffective | Effective | Ineffective |
| Preparation Example 1 | 8 | 2 | 9 | 1 |
| Preparation Example 2 | 7 | 3 | 8 | 2 |
| Preparation Example 3 | 8 | 2 | 9 | 1 |
| Preparation Example 4 | 9 | 1 | 9 | 1 |
| Comparative Preparation Example 1 | 1 | 9 | 2 | 8 |
| Comparative Preparation Example 2 | 0 | 10 | 1 | 9 |

As clearly shown in Table 2, in Preparation Examples 1 to 4 in which the ascorbic acid derivative was incorporated, high anti-inflammation analgesic effects were recognized. In contrast, in Comparative Preparation Examples 1 and 2, no effect was recognized.

Preparation Example 5

Gel

| | |
|---|---|
| Xanthan gum | 1% |
| L-3-0-Ethylascorbic acid | 3% |
| Ethanol | 10% |
| Methylparaben | 0.2% |
| Methyl salicylate | 1.0% |
| 3.0% Citric acid buffer solution | 10% |
| Purified water | Balance |

The preparation method is the same as that in Preparation Example 1.

Preparation Example 6

Gel

| | |
|---|---|
| L-3-0-Dodecylascorbic acid | 4% |
| Ethanol | 10% |
| Methylparaben | 0.2% |
| L-Menthol | 1.0% |
| 3.0% Citric acid buffer solution | 10% |
| Xanthan gum | 2% |
| Purified water | Balance |

The preparation method is the same as that in Preparation Example 1.

Preparation Example 7

Gel

| | |
|---|---|
| L-3-0-Octadecyloxycarbonylmethylascorbic acid | 5% |
| Ethanol | 10% |
| Methylparaben | 0.2% |
| Indomethacin | 0.5% |
| 3.0% Citric acid buffer solution | 10% |
| Xanthan gum | 2% |
| purified water | Balance |

The preparation method is the same as that in Preparation Example 1.

Preparation Example 8

Gel

| | |
|---|---|
| L-3-0-Dodecylcarbonylmethylascorbic acid | 5% |
| Ethanol | 10% |
| Methylparaben | 0.2% |
| Glycol salicylate | 1.0% |
| Xanthan gum | 2% |
| 3.0% Citric acid buffer solution | 10% |
| Purified water | Balance |

The preparation method is the same as that in Preparation Example 1.

Preparation Example 9

Gel

| | |
|---|---|
| Xanthan gum | 1% |
| L-3-0-Ethylascorbic acid | 3% |
| Ethanol | 10% |

Preparation Example 10
Gel

| | |
|---|---|
| Xanthan gum | 1% |
| L-3-0-Ethylascorbic acid | 3% |
| Ethanol | 10% |
| Methylparaben | 0.2% |
| L-Menthol | 1.0% |
| DL-Camphor | 1.0% |
| 3.0% Citric acid buffer solution | 10% |
| Purified water | Balance |

| | |
|---|---|
| Methylparaben | 0.2% |
| L-Menthol | 1.0% |
| Eucalyptus oil | 1.0% |
| 3.0% Citric acid buffer solution | 10% |
| Purified water | Balance |

The preparation method is the same as that in Preparation Example 1.

The preparation method is the same as that in Preparation Example 1.

preparation Example 11
Sheet

| | |
|---|---|
| Xanthan gum | 1% |
| L-3-0-Ethylascorbic acid | 3% |
| Salicylic acid | 0.5% |
| Ethanol | 10% |
| Methylparaben | 0.2% |
| Carbopol | 1% |
| Citric acid | 1% |
| Sodium citrate | 0.1% |
| Purified water | Balance |

L-3-0-Ethylascorbic acid and methylparaben were dissolved in ethanol, the rest was added, and the mixture was dissolved in purified water. The resultant gel base was spread in a non-woven fabric as a support, to obtain a sheet-like cataplasm preparation.

Preparation Example 12
Cream (A)

| | |
|---|---|
| Methyl salicylate | 1% |
| Diphenhydramine | 0.2% |
| Glycerin monostearate | 1% |
| Cetyl alcohol | 2% |
| Vaseline | 1% |
| Polyoxyethylene (20) cetyl | 3% |
| Squalane | 20% |
| Isopropyl myristate (B) | 1% |
| Glycerin | 10% |
| Sodium Citrate | 0.5% |
| L-3-0-Ethylascorbic acid | 2% |
| Ethanol | 10% |
| Methylparaben | 0.2% |
| Citric acid | 2% |
| Purified water | Balance |

Oily components (A) were heated to 70(C and mixed. Water-soluble components (B) were mixed, dissolved and then heated to 70(C, and the above oily components (A) were admixed. The admixture was emulsified with a homomixer. The emulsion was cooled to room temperature and charged into a container to obtain a cream.

Preparation Example 13
Granules

| | |
|---|---|
| L-3-0-Dodecylascorbic acid | 10% |
| Gum Arabic | 5% |
| Crystalline cellulose | 5% |
| Lactose | Balance |

Components were mixed, 5% by weight, based on the power weight, of purified water was added, and the mixture was kneaded. The kneaded wet product was granulated with an extrusion granulator, and the granulated product was dried with a tray-method dryer and classified to obtain granules.

Preparation Example 14
Tablet

Granules obtained in Example 13 were made into tablets with a direct tablet making machine.

Preparation Example 15
Injection

| | |
|---|---|
| L-3-0-Ethylascorbic acid | 100 mg |
| Saline solution for injection | 1.0 mg |

L-3-0-Ethylascorbic acid was weighed, and a saline solution for injection was added to form a solution. The solution was passed through a membrane filter having a pore size of 0.25 μm or less, the filtrate was charged in an ampoule made of glass, and the ampoule was sealed.

TEST EXAMPLE 3

Shelf lives of the anti-inflammation analgesic preparations of the present invention obtained in the above Preparation Examples 5 to 14, at 40(C for 3 months, were studied.

Table 3 showed the results. All of the anti-inflammation analgesic preparations of the present invention showed high ascorbic-acid-derivative remaining ratios and had stability.

TABLE 3

Stability

| | Ascorbic-acid-derivative remaining ratio |
|---|---|
| Preparation Example 5 | 93% |
| Preparation Example 6 | 85% |
| Preparation Example 7 | 90% |
| Preparation Example 8 | 95% |
| Preparation Example 9 | 85% |
| preparation Example 10 | 96% |
| Preparation Example 11 | 88% |
| Preparation Example 12 | 92% |
| Preparation Example 13 | 99% |
| Preparation Example 14 | 99% |
| Preparation Example 15 | 98% |

As explained above, according to the present invention, there have been provided anti-inflammation analgesic preparations containing ascorbic acid derivatives excellent in anti-inflammation analgesic effects and excellent in stabilitiy, safety and endermic absorptivity.

What is claimed is:

1. An anti-inflammation analgesic preparation comprising a 3-0-substituted ascorbic acid or a salt thereof, said 3-0-substituted ascorbic acid having the formula (II),

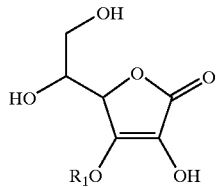

(II)

wherein
R$_1$ is ethyl and
at least one member selected from the group consisting of a salicylic acid derivative, indomethacin, piroxicam, flurbiprofen, felbinac, ketoprofen, menthol, camphor, thymol, crotamiton and eucalyptus oil.

2. A topical anti-inflammation analgesic preparation for application to skin comprising a 3-0-substituted ascorbic acid or a salt thereof, said 3-0-substituted ascorbic acid having the formula (II),

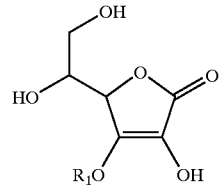

(II)

wherein
R$_1$ is ethyl and
at least one member selected from the group consisting of a salicylic acid derivative, indomethacin, piroxicam, flurbiprofen, felbinac, ketoprofen, menthol, camphor, thymol, crotamiton and eucalyptus oil.

* * * * *